United States Patent [19]

Plummer et al.

[11] Patent Number: 5,208,029
[45] Date of Patent: May 4, 1993

[54] INSECT REPELLENT AND METHOD USING PLANT OILS

[76] Inventors: Donald E. Plummer; Sonja A. Plummer, both of 10165 NW. 8th La., Ocala, Fla. 32675

[21] Appl. No.: 757,195

[22] Filed: Sep. 10, 1991

[51] Int. Cl.⁵ .............................................. A01N 65/00
[52] U.S. Cl. ................... 424/405; 424/195.1; 424/84; 424/DIG. 10; 514/919
[58] Field of Search ............... 424/84, 405, DIG. 10, 424/195.1; 514/918, 919, 729, 763, 766

[56] References Cited

U.S. PATENT DOCUMENTS

| | | | |
|---|---|---|---|
| 135,113 | 1/1873 | Goodman | 424/84 |
| 350,690 | 10/1886 | McKee | 424/195.1 |
| 4,735,803 | 4/1988 | Katz et al. | 424/195.1 |
| 4,988,508 | 1/1991 | Wilson et al. | 424/84 |
| 4,992,270 | 2/1991 | Wilson et al. | 424/84 |

OTHER PUBLICATIONS

Casida, John *Pyrethrum, The Natural Insecticide* Academic Press, 1973, pp. XVII, 138.

Foster, Catherine *The Organic Gardener* Vintage Books, N.Y., 1972, p. 59.

*Primary Examiner*—Thurman K. Page
*Assistant Examiner*—Neil S. Levy

[57] ABSTRACT

Composition for repelling insects is producted with Oil of Hedeoma Pulegioides, Oil of Pimpinella Anisum and Oil of Chrysanthemum.

5 Claims, No Drawings

INSECT REPELLENT AND METHOD USING PLANT OILS

BACKGROUND OF THE INVENTION

This invention relates to a composition for repelling insects, and more particularly relates to a composition for repelling mosquitos or blood-sucking insects using naturally found ingredients.

Many compositions have been used to repel insects including mosquitos, ticks and gnats. Most of these compositions use ingredients that may be toxic in large quantities or can be irritable to the skin of certain persons. Another drawback to many prior insect repellents is that they have an odor that is unpleasant.

SUMMARY OF THE INVENTION

An object of this invention is to provide an improved composition for repelling insects.

It is also an object of this invention to combine naturally found ingredients to create a non-irritating insect repellent.

A further object of this invention is to combine ingredients from different plants to produce a mosquito repellent that has a pleasant fragrance.

These and other objects are provided with a composition for repelling insects comprising zero to five parts by volume of Oil of Hedeoma Pulegioides; zero to sixteen parts by volume of Oil of Pimpinella Anisum; and 2,920 to 2,940 parts by volume of Oil of Chrysanthemum.

In another aspect of the invention a method for repelling biting insects is provided. In this method Oil of Chrysanthemum is provided and then applied to the skin of the subject to repel insects from the skin.

DESCRIPTION OF THE PREFERRED EMBODIMENTS

The mosquito repellent contains the ingredients shown in the following Table 1:

TABLE 1

| Ingredient | Quantity by Volume | Preferred Quantity |
|---|---|---|
| Oil of Chrysanthemum | 2,920–2,940 parts | 2,920 parts |
| Oil of *Pimpinella Anisum* (Anise Oil) | Between 1 and 70 parts | 8 parts |
| Oil of *Hedeoma Pulegioides* (Pennyroyal oil) | 1–5 parts | 4 parts |

To produce the repellent in solution, the Oil of Chrysanthemum is slowly blended with the Oil of Pimpinella Anisum and the Oil of Hedeoma Pulegioides in the proportion listed in Table 1.

Oil of Chrysanthemum by itself, without the pimpinella anisum and hedeoma pulegioides, was found to be adequate in repelling biting insects and mosquitos. The chrysanthemum oil was used by applying it to a surface area on the skin where the mosquitoes were to be repelled. However, it was found that chrysanthemum oil has a strong fragrance. By combining the three ingredients in Table 1, a mosquito repellent was produced with a light and pleasant smell that has the same properties as the chrysanthemum oil by itself.

The following are examples of testing that was conducted to determine the variations of the ingredients which were effective.

EXAMPLE 1

In Example No. 1, 2,920 parts by volume of Oil of Chrysanthemum was mixed with twelve parts by volume of Oil of Pimpinella Anisum and one part by volume of Oil of Hedeoma Pulegioides. It was found with this combination that no bites were observed in a one hour test.

EXAMPLE 2

In Example No. 2, 2,920 parts of Oil of Chrysanthemum was mixed with twenty-four parts by volume of Oil of Pimpinella Anisum and eight parts by volume of Oil of Hedeoma Pulegioides. With this combination it was observed that four bites occurred in a one hour test.

EXAMPLE 3

In Example No. 3, 2,920 parts by volume of Oil of Chrysanthemum was combined with thirty-two parts by volume of Oil of Pimpinella Anisum and sixteen parts by volume of Oil of Hedeoma Pulegioides. With this combination of ingredients it was observed that seven bites occurred in a one hour test.

EXAMPLE 4

In Example No. 4, the Oil of Chrysanthemum remained at 0.996 fluid ounces (29.20 cc) or 2,920 parts by volume and was combined with 0.24 cc, or twenty-four parts by volume of Pimpinella Anisum. The Oil of Hedeoma was varied from 0.05 cc to 0.08 ccs, i.e. five parts to eight parts by volume.

The repellent with varying quantities of Oil of Hedeoma Pulegiodes, for one hour was applied to the skin of a subject. The subject sprayed was then placed in a mosquito infested cavity and the number of mosquito bites on the skin was recorded. The results were as follows:

| Quantity of Oil of *Hedeoma Pulegiodes* | Number of Bites per Hour |
|---|---|
| .05 cc (5 parts by volume) | 0 |
| .06 cc (6 parts by volume) | 1 |
| .07 cc (7 parts by volume) | 2 |
| .08 cc (8 parts by volume) | 4 |

Accordingly, greater than five parts by volume of the Oil of Hedeoma Pulegiodes overpowered the scent of the chrysanthemum and reduced the repellant's overall effectiveness.

EXAMPLE 5

In Example No. 5, the Oil of Chrysanthemum remained at 0.996 fluid ounces. 29.20 cc or 2,920 parts and was combined with 0.05 or five parts by volume of Oil of Hedeoma Pulegioides. The Oil of Pimpinella Anisum was varied from 0.30–1.00 cc (30–100 parts by volume). The repellent with varying quantities of Oil of Pimpinella Anisum for one hour was applied to the skin of a subject. The subject sprayed was then placed in a mosquito infested cavity and the number of mosquito bites on the skin was recorded. The results were as follows:

| Quantity of Oil of *Pimpinella Anisum* | Number of Bites per Hour |
|---|---|
| 30 cc (30 parts by volume) | 0 |
| 40 cc (40 parts by volume) | 0 |
| 50 cc (50 parts by volume) | 0 |
| 60 cc (60 parts by volume) | 0 |

-continued

| Quantity of Oil of *Pimpinella Anisum* | Number of Bites per Hour |
| --- | --- |
| 70 cc (70 parts by volume) | 1 |
| 80 cc (80 parts by volume) | 2 |
| 90 cc (90 parts by volume) | 3 |
| 100 cc (100 parts by volume) | 5 |

Accordingly, 70 or greater parts by volume of Pimpinella Anisum overpowered the scent of the chrysanthemum and reduced the repellents overall effectiveness.

Various other testing was done with the preferred quantities of the solution listed in Table 1 above to determine the effectiveness of the mosquito repellent. The repellent was applied to the skin of the subject under the following conditions. The results of those tests were as follows:

TEST 1

The location of the test area was a horse farm in northwest Marion County, Fla. surrounded by pasture and wooded areas with moderate mosquito activity. The subjects were adult males and the areas temperatures in which the subject was subjected ranged from 70°-90° F., with moderate rainfall in afternoons.

TEST RESULTS: Subjects applied solution to exposed skin areas in small dabs (as one would apply perfume). Mosquitos buzzed within approximately twelve inches of the subject, but no bites were noted for six hours.

TEST 2

The location of the test area was a home located in northwest Marion County, Fla. adjoining pasture area with high grass and water standing in troughs. The area had heavy mosquito activity. Temperature of the area ranged from 70°-90° F., rainfall in afternoons. The subjects were a middle-aged female and an elderly female.

TEST RESULTS: Solution was applied as a perfume and one bite occurred on leg area. The solution was then reapplied and lightly spread on all the subjects' exposed skin surfaces. No bites for occurred for six hours.

TEST 3

The location of the test area was a mobile home located in wooded area of Marion County, Florida. The area had heavy mosquito activity in the evenings and throughout the night. The subject was a female in her early 60's who slept with her windows open.

TEST RESULTS: The subject applied the solution heavily to legs, arms, neck and face just before retiring. The subject slept comfortably throughout the night with no reported bites.

TEST 4

The location of the test area was a newly developing area of Marion County, Fla. with open fields. The subjects were bothered by gnats and biting flies while mowing property. The subjects were adult males in their mid-60's.

TEST RESULTS: The subjects applied solution from the palms of their hands and rubbed it on exposed skin surfaces. Gnats and biting insects encircle the subjects but did not bite the subjects. The solution was effective for five to six hours.

TEST 5

The location of the test area was a lake front home with heavy mosquito activity. The subjects were a middle-aged male and a middle-aged female. The solution was also applied to young adults, male and female, as well as children under twelve.

TEST RESULTS: The subjects enjoyed lawn work during the evening hours. The solution was applied from a roll-on device. The subjects were able to stay out during evening hours without annoying bites from insects.

TEST 6

The location of the test area was Lee County, Fla. in a marshy area. The subjects were a young adult male, a young adult female and a small child under five.

TEST RESULTS: The solution proved successful when applied to exposed skin surfaces of the subjects for four to six hours. The subjects also tested the formula with mineral oil added to the solution.

TEST 7

The location of the test area was a panhandle area of Florida. The subjects were adult males hunting game in wooded areas.

TEST RESULTS: The solution was applied from a roll-on to exposed skin areas of the subjects. The subjects reported excellent results for four to six hours. The subjects also confirmed that the fragrance of the solution does not affect game. Their hunting was successful.

TEST 8

The location of the test area was a farming area near the vicinity of Detroit, Mich. The subjects were a young adult female and children under twelve.

TEST RESULTS: The subjects reported using the solution from a roll-on and did not have any bites while picking strawberries on the farm.

Anisum oil is produced from dried ripe fruit of an annual Umbelliferous plant (*Pimpinella anisum* L.). Further details of this plant and the constituents and characteristics of Oil of Pimpinella Anisum are described in *The Source Book of Flavors*, written by Henry Heath, published by A.V.I. of Westport, Conn., 1981, p. 220, which is hereby incorporated by reference. The constituents of pennyroyal oil is described in *The Source Book of Flavors*, p. 217. Pennyroyal oil is obtained by steamed distillation from the fresh or partly dried plant *Mentha pulegium* L. (Fam. Labiatae). The Oil of Chrysanthemum is distilled from a chrysanthemum flower and is available commercially as pure chrysanthemum oil from Technology Flower and Fragrances of Saddlebrook, N.J.

This concludes the description of the preferred embodiments. A reading by those skilled in the art will bring to mind various changes without departing from the spirit and scope of the invention. It is intended, however, that the invention only be limited by the following appended claims.

What is claimed is:

1. A composition for repelling biting mosquitoes comprising:
   one to five parts by volume of Oil of Hedeoma Pulegioides;
   between 1 and 70 parts by volume Oil of Pimpinella Anisum; and 2,920 to 2,940 parts by volume Oil of Chrysanthemum.

2. The composition as recited in claim 1 wherein said Oil of Hedeoma Pulegiodes is present in an amount of four to five parts by volume.

3. The composition as recited in claim 1 wherein said Oil of Chrysanthemum is present in an amount of 2,920 parts by volume.

4. The composition as recited in claim 1 wherein said Oil of Pimpinella Anisum is present in an amount of about eight parts by volume.

5. A method for repelling biting mosquitoes comprising the steps of blending 30–60 parts of Oil of Pimpinella Anisum, 1–5 parts of Oil of Hedeoma Pulegioides and 2,920–2,940 parts of Oil of Chrysanthemum, all by volume and applying the blend to the skin of a subject to repel mosquitoes from the skin.

* * * * *